(12) United States Patent
Chen et al.

(10) Patent No.: US 9,447,149 B2
(45) Date of Patent: Sep. 20, 2016

(54) METHODS AND COMPOSITIONS FOR THE RAPID SYNTHESIS OF RADIOMETAL-LABELED PROBES

(71) Applicant: University of Southern California, Los Angeles, CA (US)

(72) Inventors: Kai Chen, San Gabriel, CA (US); Peter Stephen Conti, Pasadena, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 0 days.

(21) Appl. No.: 13/787,781

(22) Filed: Mar. 6, 2013

(65) Prior Publication Data

US 2013/0237686 A1    Sep. 12, 2013

Related U.S. Application Data

(60) Provisional application No. 61/607,433, filed on Mar. 6, 2012.

(51) Int. Cl.
| | |
|---|---|
| *A61K 38/12* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 7/64* | (2006.01) |

(52) U.S. Cl.
CPC ....................................... *C07K 7/64* (2013.01)

(58) Field of Classification Search
CPC .................... A61K 51/088; A61K 51/0482
See application file for complete search history.

(56) References Cited

PUBLICATIONS

Zeng et al., J Nucl Med. 2011; 52 (Supplement 1):576.*
Pierce Protein Research Products, Thermo Scientific, Previews, 2008, vol. 12, issue 2, product #21581.*
Kolb et al., Peptide Labelling Strategies S67, Jun. 15, 2009 created and modified on Dec. 14, 2010.*
Ma et al., Bioconjugate Chem., 2011, 22, 2093-2103.*
Carpenter et al., Med. Chem. Lett., 2011, 2, 885-889.*
Cai et al., Nuclear Medicine and Biology, 2007, 37, 57-65.*

* cited by examiner

*Primary Examiner* — James H Alstrum Acevedo
*Assistant Examiner* — Kaipeen Yang
(74) *Attorney, Agent, or Firm* — DLA Piper LLP (US)

(57) ABSTRACT

The present application is directed to rapid and efficient synthesis of radiometal-labeled probes, pharmaceutical compositions comprising radiometal-labeled probes, and methods of using the radiometal-labeled probes. Such radiometal-labeled probes can be used in imaging studies, such as Positron Emitting Tomography (PET) or Single Photon Emission Computed Tomography (SPECT), and therapy studies.

7 Claims, 6 Drawing Sheets

METHODS AND COMPOSITIONS FOR THE RAPID SYNTHESIS OF RADIOMETAL-LABELED PROBES

FIELD OF THE INVENTION

The present invention is generally directed to method and compositions for the rapid synthesis of radiometal-labeled probes.

BACKGROUND OF THE INVENTION

Radiopharmaceuticals are radioactive drugs which can have either diagnostic or therapeutic applications. In diagnostic nuclear medicine, the radionuclide is used as a tracer to provide functional information about the tissue under investigation [1-2]. In contrast, therapeutic radionuclides should have particulate radiations with an in vivo range sufficient to destroy the target tissue but not so long as to cause collateral damage. The nuclear requirements for either diagnosis or therapy are seldom met by the radionuclides of the biologically ubiquitous elements such as C, H, N, O, etc., but oblige the use of biologically unimportant elements, almost all of which are metallic. For example, several non-conventional metallic radionuclides, such as $^{64}$Cu, $^{86}$Y, and $^{89}$Zr, have been applied to positron emission tomography (PET) probes [3]. These metallic PET isotopes are usually characterized by longer half-lives, allowing the evaluation of radiopharmaceutical kinetics in same subject to be achieved by successful PET imaging over several hours or even days. Among these metallic radionuclides, $^{64}$Cu ($t_{1/2}$=12.7 h; $\beta^+$ 655 keV, 17.8%) has attracted considerable interest because of its favorable decay half-life, low $\beta^+$ energy, and commercial availability [4].

Click chemistry offers chemists a platform for general, modular and high yielding synthetic transformations for constructing highly diverse molecules [5]. The Huisgen 1,3-dipolar cycloaddition reaction, which fuses an azide and an alkyne together, and provides access to a variety of five-membered heterocycles, has become of great use in labeling studies, the development of new therapeutics and nanoparticles, and in protein modification [6]. However, the Huisgen 1,3-dipolar cycloaddition reaction often requires the presence of catalytic amounts of non-radiolabeled Cu(I) ions, which interfere with radiometals and make click reaction impossible for the direct construction of radiometal-labeled probes.

To the best of our knowledge, the catalyst-free click reaction has not yet been employed in the radiometal-labeled probes.

SUMMARY OF THE INVENTION

One embodiment of the present invention is directed to a rapid, efficient, and catalyst-free method for generating radiometal-labeled probes and method of imaging integrin receptors (specifically, Integrin $\alpha_v\beta_3$) in vivo with the radiometal-labeled cyclopeptide derivatives.

Another embodiment of the present invention utilizes a Huisgen 1,3-dipolar cycloaddition reaction including an aza-dibenzocyclooctyne ligation to assemble radiometal-labeled probes with various hydrophilic linkages, such as polyethelene glycol units and other sugar mimetics. This synthetic method is characterized by its rapidity (<15 min) and excellent yield (>98%) without adding of any catalysts. It is not possible to use a catalyst-free methodology for preparing radiometal-labeled probes using conventional Huisgen 1,3-dipolar cycloaddition reaction. The newly developed cyclopeptide derivatives obtained using the methods described herein maintain good binding affinity to integrin $\alpha_v\beta_3$ receptor, and have excellent tumor uptake and favorable pharmacokinetic behavior.

Another embodiment of the present invention is a fast and efficient for radiometal-labeling using catalyst-free click chemistry, and its application to the synthesis of a $^{64}$Cu-labeled derivative of cyclic RGD peptide [c(RGDfK)](FIG. 1), an integrin $\alpha_v\beta_3$ ligand [8]. The so-called "click" probe maintains good binding affinity to integrin $\alpha_v\beta_3$ receptor, and exhibits excellent tumor targeting and retention properties in an integrin $\alpha_v\beta_3$-positive mouse tumor model.

Another embodiment of the present invention is a new catalyst-free click chemistry approach based on aza-dibenzocyclooctyne ligation has been developed for radiometal-labeling of biomolecules. The reaction proceeds with fast rates, making it an attractive radiometal-labeling method at low concentration. Our technique is novel and general, and can be applied to other radiometal-labeled probes for imaging and therapy applications.

One embodiment of the present invention is directed to a rapid, efficient, and catalyst-free click chemistry method for generating radiometal-labeled probes for imaging and therapy according to Formula III comprising: reacting an azido composition, $N_3$-L (Formula I, below) with a strained alkyne (Formula II, below) as shown in the following Reaction (Reaction 1):

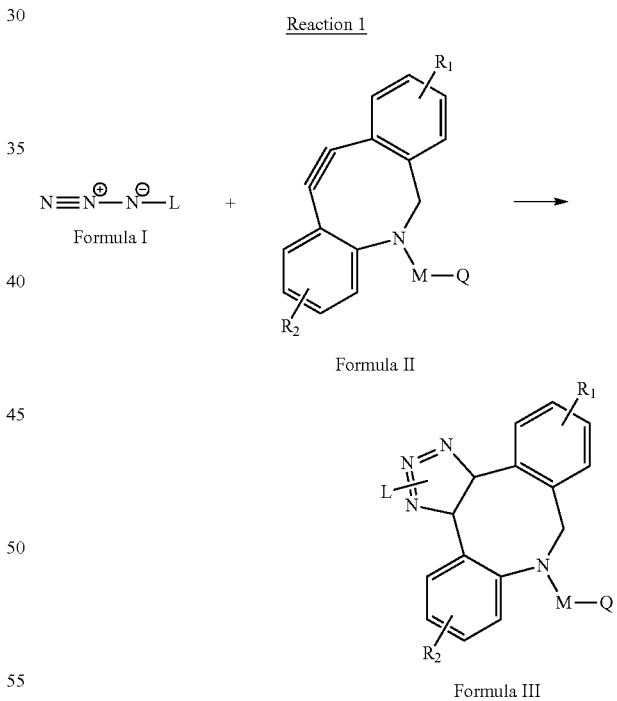

wherein L may be conjugated to any of the nitrogen atoms of the triazole moiety, wherein L includes at least one biological component, including without limitation a small molecule, peptide, protein and/or nanoparticle, or alternatively, L is a chelator capable of coordinating a radiometal nuclide, the moiety M is an optional linker moiety, but when included may comprise one or more hydrophilic groups, including, for example, one or more polyethelene glycol units, one or more sugars, the moiety Q is a chelator capable of coordinating a radiometal nuclide, or alternatively, if L is a chelator, Q includes at least one biological component, including without limitation a small molecule, peptide, protein and/or nanoparticle, and Another embodiment of the present invention is directed to a cyclopeptide derivative of the following Formula IV.

Formula IV

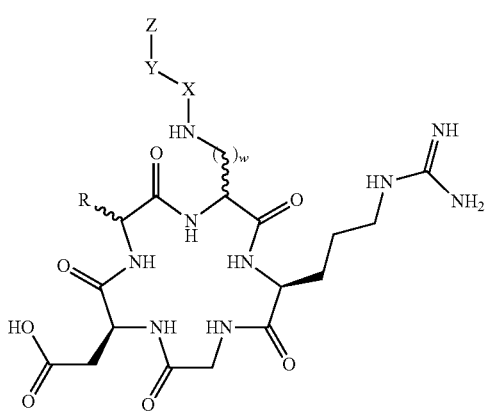

wherein at least on of moieties X, Y and Z includes a click chemistry linkage, such as a triazole moiety, wherein R is selected from the group consisting of a side chain of a natural amino acid and a side chain of an unnatural amino acid, wherein the natural amino acid and the unnatural amino acid is either in the D or L form;

wherein X is a heterocycle or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

wherein Y is a heterocycle, or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

wherein Z is a heterocycle, or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

wherein w is 1, 2, 3, 4, or 5; and wherein any one of X, Y, and Z comprises a radiometal nuclide, including, but not limited to the following: $^{61}$Cu, $^{62}$Cu, $^{64}$Cu, $^{67}$Cu, $^{68}$Ga, $^{86}$Y, and $^{89}$Zr. In a first preferred embodiment, Y is a heterocycle; and X is a linker either comprising a sugar mimetic selected from the group consisting of a 4 to 6-membered carbocycle substituted with at least one hydroxyl group and a 5- to 6-membered heterocycle substituted with at least one hydroxyl group or comprising a sugar moiety selected from the group consisting of glucose and galactose.

DETAILED DESCRIPTION OF THE INVENTION

Definitions

Figure 1:
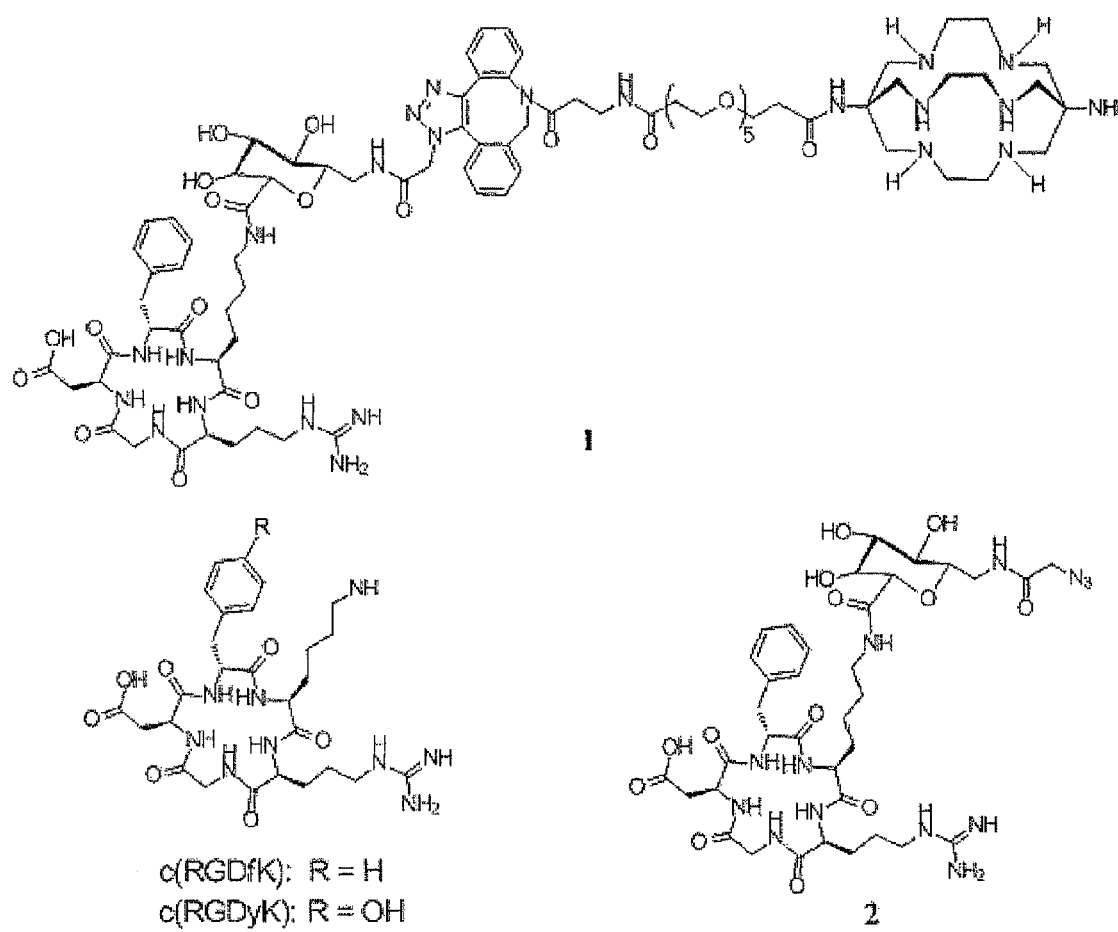
FIG. 1 illustrates the chemical structures of several RGD peptides.

The term "alkyl" means a straight or branched chain acyclic saturated hydrocarbon. The term "C$_1$-C$_6$ alkyl" herein used means C$_1$-C$_6$ straight or branched chain alkyl, for example, methyl, ethyl, n-propyl, i-propyl, n-butyl, butyl, sec-butyl, tert-butyl, n-pentyl, i-pentyl, neo-pentyl, tert-pentyl, and the like.

The term "alkenyl" refers to a branched or unbranched hydrocarbon having at least one carbon-carbon double bond. The term "C$_{2-6}$-alkenyl" refers to a hydrocarbon having two to seven carbon atoms and comprising at least one carbon-carbon double bond.

The term "alkynyl" refers to a branched or unbranched hydrocarbon having at least one carbon-carbon triple bond. The term "C$_{2-6}$-alkynyl" refers to a hydrocarbon having two to seven carbon atoms and comprising at least one carbon-carbon triple bond.

The term "carbocycle" refers to a non-aromatic stable 3- to 8-membered carbon ring which may be saturated, mono-unsaturated or poly-unsaturated. The carbocycle may be attached at any endocyclic carbon atom which results in a stable structure. Preferred carbocycles have 5-7 carbons.

The term "aryl" herein used means monocyclic or condensed ring aromatic hydrocarbons. Examples of the aryl are phenyl, naphthyl, and the like.

The term "heterocycle" as used herein is intended to mean monocyclic, spirocyclic, bicyclic or tricyclic ring of up to 10 atoms in each ring, wherein each ring is aromatic or non-aromatic and contains carbon and from 1 to 4 heteroatoms selected from the group consisting of O, N, P and S. A nonaromatic heterocycle may be fused with an aromatic aryl group such as phenyl or aromatic heterocycle.

The term "halogen" herein used means fluoro, chloro, bromo, and iodo.

The term "hydroxy" as used herein, means an —OH group.

The term "nitro" as used herein, means a —NO$_2$ group.

The term "carbonyl" as used herein, means a —C(O)— group.

The term "sulfonamide" refers to the group —SO$_2$NH$_2$.

The term "sulfonic acid" and "sulfonate" refers to the group SO$_3$H, or a and an acceptable salt or ester thereof, respectively.

The term "phosphate" refers to an ester of phosphoric acid, and includes salts of a phosphate moiety.

The term "amine" includes primary, secondary, and tertiary amines having, e.g., the formula N(group)3 wherein each group can independently be H or non-H, such as alkyl, aryl, and the like. Amines include but are not limited to RNH$_2$, for example, alkylamines, arylamines, alkylarylamines; R2NH wherein each R is independently selected, such as dialkylamines, diarylamines, aralkylamines, heterocyclylamines and the like; and R3N wherein each R is independently selected, such as trialkylamines, dialkylarylamines, alkyldiarylamines, triarylamines, and the like. The term "amine" also includes ammonium ions as used herein.

The term "alkoxy" denotes straight chain or branched alkoxy, preferably C$_{1-6}$ alkoxy. Examples of alkoxy include methoxy, ethoxy, n-propoxy, isopropoxy and the different butoxy isomers.

The term "optionally substituted" means the addition of a substituent group to the composition that is referred to. Suitable substituents include hydroxy, alkoxy (e.g., methoxy and ethoxy), mercapto, alkylthio (e.g., methylthio), cycloalkyl (e.g., cyclopropyl, cyclobutyl, cyclopentyl, and cyclohexyl), halogen (e.g., fluoro, chloro, bromo, and iodo), carboxy, alkoxycarbonyl (e.g., methoxycarbonyl and ethoxycarbonyl), nitro, cyano, haloalkyl (e.g., trifluoromethyl), substituted or unsubstituted amino (e.g., methylamino, dimethylamino, and carbamoylamino), guanidino, phenyl, benzyloxy, and the like. These substituents are able to bind them at one or more of any possible positions As used herein, the term "hydrophilic moiety," is any anionic, cationic, zwitterionic, or nonionic group that is polar. Nonlimiting examples include anionics such as sulfate, sulfonate, carboxylic acid/carboxylate, phosphate, phosphonates, and the like; cationics such as: amino, ammonium, including mono-, di-, and trialkylammonium species, pyridinium, imidazolinium, amidinium, poly(ethyleneiminium), and the like; zwitterionics such as ammonioalkylsulfonate, ammonioalkylcarboxylate, amphoacetate, and the like; and nonionics such as hydroxyl, sulfonyl, ethyleneoxy, amido, ureido, amine oxide, and the like.

The term "sugar moiety" means monosaccharides (e.g., glucose, arabinose, fucose, galactose, mannose, xylose, fructose, lyxose, allose, arinose, ribose, talose, gulose, idose, altrose, sorbitol, mannitol or glucosamine), disaccharides and oligosaccharides (e.g., maltose, isomaltose, turanose, gentiobiose, melibiose, planteobiose, primererose, vicianose, nigerose, laminaribiose, rutinose, cellobiose, xylobiose, maltotriose, gentianose, melezitose, planteose, ketose, trehalose, sucrose, lactose, raffinose or xylobiose), polysaccharides (e.g., amylose, ficol, dextrin, starch, dextran, polydextrose, pullulan, cyclodextrin, glucomannoglycan, glucomannan, guar gum, gum arabic or glycosaminoglycan), complex carbohydrates (e.g., glycopeptide, glycoprotein, glycolipid or proteoglycan), and the like.

The term "PEG" is used broadly to encompass any polyethylene glycol molecule, without regard to size or to modification at an end of the PEG, and can be represented as linked to the FGF-21 polypeptide by the formula: XO—(CH$_2$CH$_2$O)$_n$—CH$_2$CH$_2$—Y where n is 2 to 10,000 and X is H or a terminal modification, including but not limited to, a C$_{1-6}$ alkyl, a protecting group, or a terminal functional group.

As used herein, the term "PEG moiety" is intended to include, but is not limited to, linear and branched PEG, methoxy PEG, hydrolytically or enzymatically degradable PEG, pendant PEG, dendrimer PEG, copolymers of PEG and one or more polyols, and copolymers of PEG and PLGA (poly(lactic/glycolic acid)) and the like. According to the present invention, the term polyethylene glycol or PEG is meant to comprise native PEG as well as derivatives thereof.

The term "natural amino acid" refers to one of the twenty commonly occurring amino acids. Natural amino acids can be in their D or L form. For example, a natural amino acid can be selected from the group consisting of L-alanine, L-arginine, L-asparagine, L-aspartic acid, L-cysteine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, L-valine, and mixtures thereof. In some cases, an amino acid is selected from L-glycine and L-aspartic acid. The term "unnatural amino acid" is any amino acid that is not a natural amino acid.

As used herein, the term "polar amino acid moiety" refers to the side chain of a polar natural or unnatural amino acid. Polar natural amino acids include, but are not limited to, arginine, asparagine, aspartic acid, cysteine, glutamic acid, glutamine, histidine and lysine.

The term "peptide" is a sequence of 2 to 25 amino acids (e.g. as defined hereinabove) or peptidic residues having one or more open valences. The sequence may be linear or cyclic. For example, a cyclic peptide can be prepared or may result from the formation of disulfide bridges between two cysteine residues in a sequence. A peptide can be linked through the carboxy terminus, the amino terminus, or through any other convenient point of attachment, such as, for example, through the sulfur of a cysteine. Peptide derivatives can be prepared as disclosed in U.S. Pat. Nos. 4,612,302; 4,853,371; and 4,684,620. Peptide sequences specifically recited herein are written with the amino terminus on the left and the carboxy terminus on the right.

The term "polypeptide" refers to a biopolymer compound made up of a single chain of amino acid residues linked by peptide bonds. The term "protein" as used herein may be synonymous with the term "polypeptide" or may refer, in addition, to a complex of two or more polypeptides.

As used herein, reference to "Arg-Gly-Asp peptide" or "RGD peptide" is intended to refer to a peptide having one or more Arg-Gly-Asp containing sequence which may function as a binding site for a receptor of the "Arg-Gly-Asp family of receptors", e.g., an integrin. The sequence RGD is present in several matrix proteins and is the target for cell binding to matrix by integrins. Platelets contain a large amount of RGD-cell surface receptors of the protein GP II$_b$/III$_a$, which is primarily responsible, through interaction with other platelets and with the endothelial surface of injured blood vessels, for the development of coronary artery thrombosis. The term RGD peptide also includes amino acids that are functional equivalents (e.g., RLD or KGD) thereof provided they interact with the same RGD receptor. Peptides containing RGD sequences can be synthesized from amino acids by means well known in the art, using, for example, an automated peptide synthesizer, such as those manufactured by Applied Biosystems, Inc., Foster City, Calif.

The term "chelate" may be used as a noun or a verb. As a noun, "chelate" refers to one or more atoms that are either capable of chelating one or more metal ions, or are chelating to one or more metal ions. In some embodiments, only one metal ion coordinates to a chelate. A chelator refers to compound comprising a chelate that is a) capable of chelating to one or more metal ions or b) are coordinated to (or chelated to) to one or more metal ions. Typically, just one metal ion is chelated to a chelator.

The term "linker" means any chemical group positioned between different segments of the compounds of the present invention. These chemical groups may be of any stable chemical structure, and may provide spacing between segments, impart conformational constraints on the segments, provide drug targeting or drug delivery functionality, increase absorption and/or lifespan in vivo, or provide any additional ancillary role that benefits the utility of the molecule. Examples include, but are not limited to, methylene —$(CH_2)_n$— units, polyethylene glycol or other biopolymeric molecules, sugar or moieties, natural products, peptide-nucleic acid (PNA) molecules, both natural and unnatural amino acids and nucleic acids.

A copper-free click reaction was reported by Ning et al. (2010, Angew Chem Int; Ed 49:3065-68), involving strain-promoted alkyne-nitron cycloaddition. To address the slow rate of the original cyclooctyne reaction, electron-withdrawing groups are attached adjacent to the triple bond (Id.) Examples of such substituted cyclooctynes include difluorinated cyclooctynes, 4-dibenzocyclooctynol and azacyclooctyne (Id.)

One embodiment of the present invention is directed to a rapid, efficient, and catalyst-free click chemistry method for generating radiometal-labeled probes for imaging and therapy according to Formula III comprising: reacting an azido composition, $N_3$-L (Formula I, below) with a strained alkyne (Formula II, below) as shown in the following Reaction (Reaction Scheme 1):

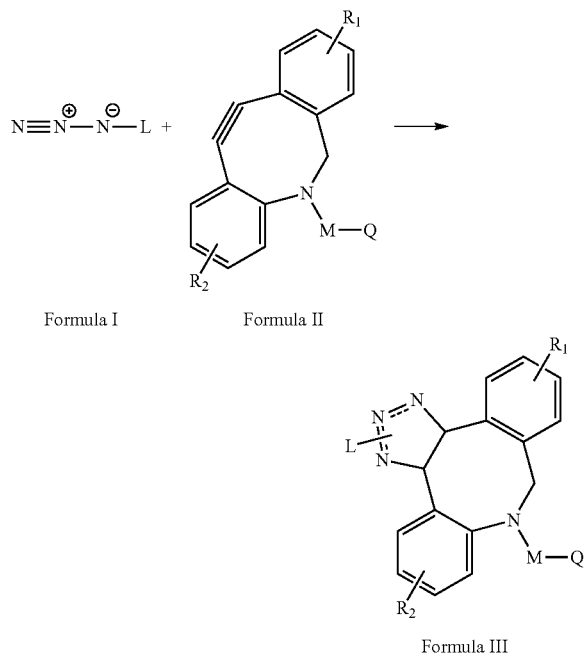

wherein L may be conjugated to any of the nitrogen atoms of the triazole moiety, wherein L includes at least one biological component, including without limitation a small molecule, peptide, protein and/or nanoparticle, or alternatively, L is a chelator capable of coordinating a radiometal nuclide, the moiety M is an optional linker moiety, but when included may comprise one or more hydrophilic groups, including, for example, one or more polyethelene glycol units, one or more sugars, the moiety Q is a chelator capable of coordinating a radiometal nuclide, or alternatively, if L is a chelator, Q includes at least one biological component, including without limitation a small molecule, peptide, protein and/or nanoparticle, and In Formula II, the benzene rings may be mono-, di-, tri-, or tetra-substituted with $R_1$ and $R_2$ groups selected from the group consisting of H, halide, hydroxy, alkyl, aryl, nitro or amine groups. In a preferred embodiment, chelator is chelated to a radiometal nuclide which may including, but is not limited to the following: $^{61}Cu$, $^{62}Cu$, $^{64}Cu$, $^{67}Cu$, $^{68}Ga$, $^{86}Y$, and $^{89}Zr$.

Another embodiment of the present invention is directed to a cyclopeptide derivative of the following Formula IV.

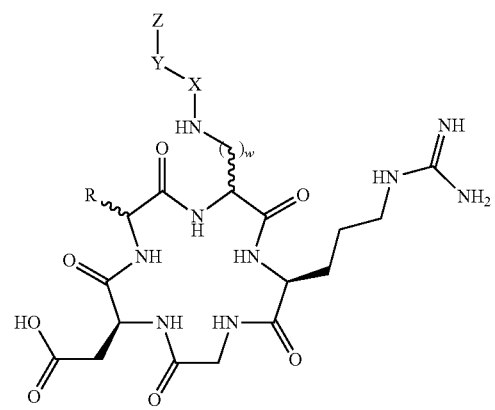

Formula IV wherein at least on of moieties X, Y and Z includes a click chemistry linkage, such as a triazole moiety, wherein R is selected from the group consisting of a side chain of a natural amino acid and a side chain of an unnatural amino acid, wherein the natural amino acid and the unnatural amino acid is either in the D or L form;

wherein X is a heterocycle or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

wherein Y is a heterocycle, or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

wherein Z is a heterocycle, or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

wherein w is 1, 2, 3, 4, or 5; and wherein any one of X, Y, and Z comprises a radiometal nuclide, including, but not limited to the following: $^{61}Cu$, $^{62}Cu$, $^{64}Cu$, $^{67}Cu$, $^{68}Ga$, $^{86}Y$, and $^{89}Zr$. In a first preferred embodiment, Y is a heterocycle; and X is a linker either comprising a sugar mimetic selected from the group consisting of a 4 to 6-membered carbocycle substituted with at least one hydroxyl group and a 5- to 6-membered heterocycle substituted with at least one hydroxyl group or comprising a sugar moiety selected from the group consisting of glucose and galactose.

In a second preferred embodiment, Y is a heterocycle;

X is selected from the group consisting of:

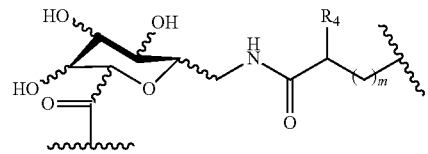
Formula V

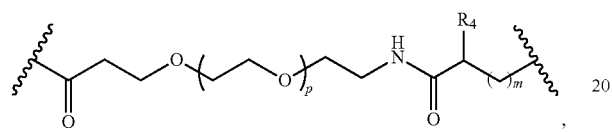
Formula VI

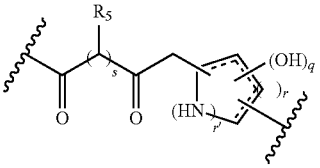
Formula VII

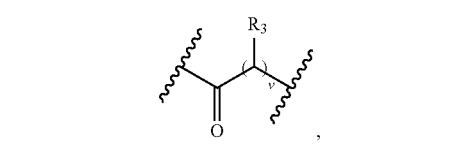
Formula VIII

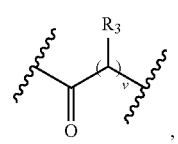
Formula IX

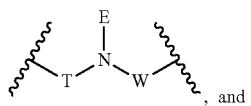
Formula X

Z is selected from the group consisting of:

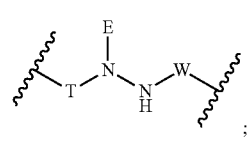
Formula V

Formula VI

-continued

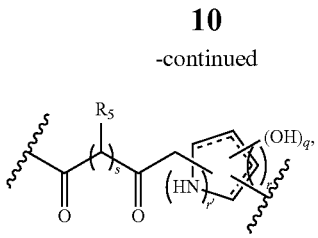
Formula VII

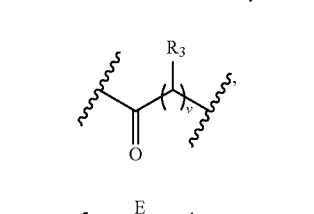
Formula VIII

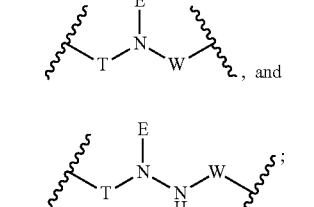
Formula IX

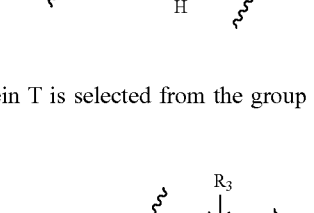
Formula X wherein T is selected from the group consisting of:

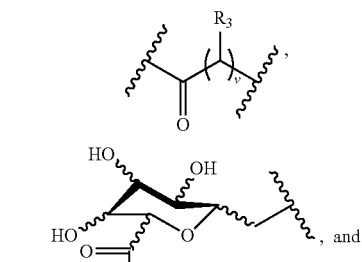

wherein W is selected from the group consisting of:

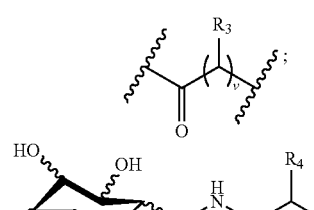

wherein E is selected from the group consisting of:

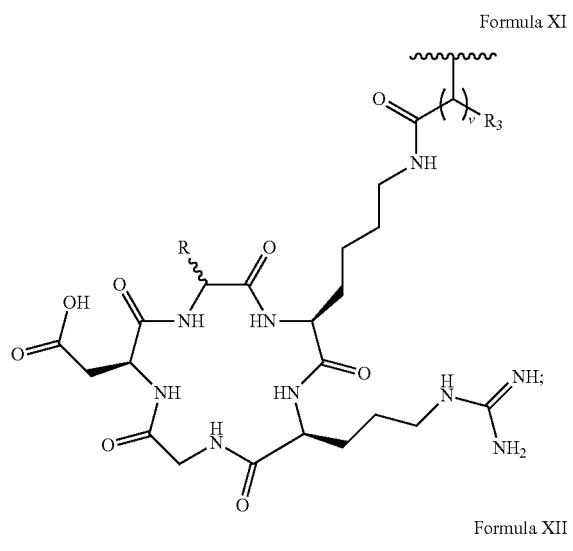

Formula XI

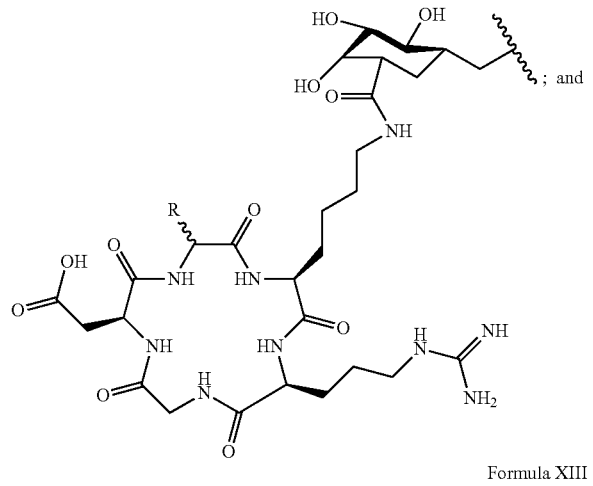

Formula XII

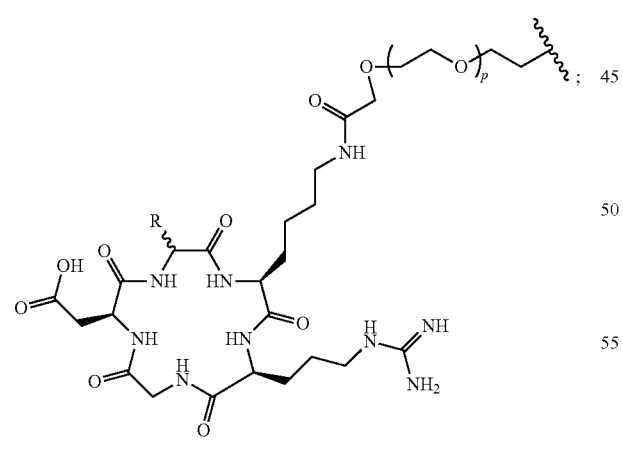

Formula XIII each R is independently selected from the group consisting of a side chain of a natural amino acid and a side chain of an unnatural amino acid, wherein the natural amino acid and the unnatural amino acid is either in the D or L form;

each $R_3$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

each $R_4$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle, and heterocycle, groups are each optionally substituted;

each $R_5$ is independently selected from the group consisting of —H, —OH, $C_1$-$C_6$ alkyl, $C_2$-$C_6$ alkenyl, $C_2$-$C_6$ alkynyl, $C_1$-$C_6$ alkyloxy, aryl-($C_1$-$C_6$ alkylene)-, hydroxy-$C_1$-$C_6$-alkyl, and $C_1$-$C_6$-alkoxy-$C_1$-$C_6$-alkyl, wherein the alkyl, alkenyl, alkynyl, alkyloxy, and aryl-alkylene groups are each optionally substituted;

each v is 0, 1, 2, 3, or 4;
m is 0, 1, 2, 3 or 4;
p is an integer between 1 and 110;
q is 1, 2, 3 or 4;
r is 1, 2 or 3;
r' is 0 or 1;
s is 1, 2, 3 or 4; and
the radionuclide is selected from a radiometal nuclide, including, but not limited to the following: $^{61}$Cu, $^{62}$Cu, $^{64}$Cu, $^{67}$Cu, $^{68}$Ga, $^{86}$Y, and $^{89}$Zr.

wherein the configuration of the chiral centers may be R or S or mixtures thereof.

In another preferred embodiment, R is a side chain of a natural amino acid;

X is

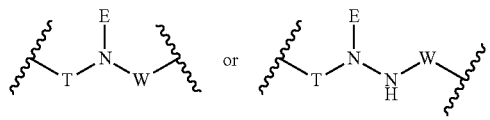

Wherein the variables T, E, W;
Y is 3a,8,9,13b-tetrahydro-3H-dibenzo[b,f][1,2,3]triazolo[4,5-d]azocine; and
Z is selected from the group consisting of:

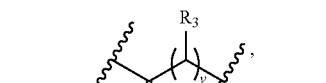

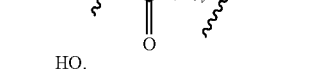

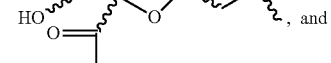

$R_3$ is selected from the group consisting of —H, $C_1$-$C_6$ alkyl, $C_2$-$C_6$ alkenyl, and $C_2$-$C_6$ alkynyl, wherein the alkyl, alkenyl, and alkynyl groups are each optionally substituted; and any one of X, Y, and Z comprises a radiometal nuclide including, but not limited to the following: $^{61}$Cu, $^{62}$Cu, $^{64}$Cu, $^{67}$Cu, $^{68}$Ga, $^{86}$Y, and $^{89}$Zr.

Preferably, a portion of the peptide contains a primary amine group, such as a lysine residue, which is utilized for conjugation to moiety XYZ. The configuration of C-α of the amine-containing residue may be R or S. Preferably, the moiety XYZ contains zero, one, or more hydrophilic groups (such as hydroxyl, sulfonate, phosphate, etc.).

Preferably, the nuclide label A is covalently conjugated to one or more of X, Y, and Z.

Another embodiment of the present invention is directed to a method for preparing a radiopharmaceutical comprising reacting an azido compound formula $N_3$-L with a strained alkyne to form of a 1,2,3-triazole under reaction conditions that do not include a catalyst. Preferably, the strained alkyne has a formula according to Formula II, and the benzene rings may be mono-, di-, tri-, or tetra-substituted with $R_1$ and $R_2$ groups selected from the group consisting of H, halide, hydroxy, alkyl, aryl, nitro or amine groups. Preferably, L is cyclopeptide and the strained alkyne is capable of being coupled to a chelator. Preferably, the strained alkyne is coupled to a chelator prior to reaction with the azido compound to form an alkyne-containing chelator. Preferably, the alkyne-containing chelator is labeled by a radiometal prior to reaction with the azido compound. The radiometal may be selected from the group consisting of $^{61}Cu$, $^{62}Cu$, $^{64}Cu$, $^{67}Cu$, $^{68}Ga$, $^{86}Y$, and $^{89}Zr$.

Another embodiment of the present invention is a method of modifying an RGD-sequence containing cyclic peptide with the moiety XYZ, which installs a nuclide label on the cyclic peptide, comprising: click chemistry.

A catalyst-free click chemistry approach in accordance with the present invention, describes the rapid, selective and specific formation of 1,2,3-triazoles starting from an azide and a strained alkyne moiety. An azido group can be attached to the cyclopeptide while a strained alkyne moiety can be coupled with a chelator. Afterwards, the alkyne-containing chelator can be labeled by a radiometal, and followed by a rapid assembling with azido-containing piece to form the final radiometal-labeled probes without adding of any catalysts. The hydrophilic linkages can also be readily incorporated into the final product. Because of this high-yielding and modular approach, the pharmacokinetic properties of final radiometal-labeled probes are easily modified.

One embodiment of the present invention is a catalyst-free click chemistry approach to rapidly yet efficiently construct a $^{64}Cu$-labeled cyclopeptide for PET imaging of integrin $\alpha_v\beta_3$ receptor in vivo. Various aspects and embodiments are discussed in relation to the $^{64}Cu$-labeled cyclopeptide described herein, and other aspects and embodiments will be apparent to those skilled in the art. The various aspects and embodiments disclosed herein are for purposes of illustration and are not intended to be limiting. Those skilled in the art will recognize, or be able to ascertain using no more than routine experimentation, many equivalents to the specific embodiments of the method and compositions described.

In a preferred embodiment, a suitable azide moiety containing RGD peptide is selected. One of ordinary skill in the art can modify the RGD peptide according a particular application. For instance, in one embodiment, it was found that glycosylation on the lysine side chain of cyclic RGD peptides decreased lipophilicity and hepatic uptake [9]. This finding prompted us to consider methods for preparing azido galacto-RGD peptide. To this end, compound 2 as shown in FIG. 1. The fully protected c[R(Pbf)GD(O$^t$Bu)fK] peptide was conjugated with Fmoc-protected galactose, followed by deprotection of the Fmoc group, azido acetic acid coupling, and guanidine and acid deprotections. The synthesis was achieved in four steps with a total yield of 44%. Compound 2 was obtained in a great chemical purity (>95%) without HPLC purification.

In a preferred embodiment, a suitable $^{64}Cu$-chelator complex system, which can be readily conjugated with a strained alkyne should be selected. Suitable bifunctional chelators useable with the invention include oxygen and nitrogen containing cyclic chelators known to those of ordinary skill. Various bifunctional chelators (BFCs) are useable in connection with the present invention, including cyclam ((1,4,8,11-tetraazacyclotetradecane) and cyclen (1,4,7,10-tetraazacyclododecane) backbone-based chelators and cross-bridged tetraamine ligands, all of which have been developed for $^{64}Cu$ labeling [4, 10]. Suitable BFCs include cage-like hexaazamacrobicyclic sarcophagine (Sar), has gained great attention as potential $^{64}Cu$ chelators. We and others demonstrated that either one of the inert primary amines of 3,6,10,13,16,19-hexaazabicyclo[6.6.6]eicosane-1,8-diamine (DiAmSar) or both primary amines could be modified and coupled with biologically relevant ligands[11]. The resulting $^{64}Cu$ complexes present improved in vivo stability and radiolabeling efficiency. On the other hand, an aza-dibenzocyclooctyne system has been proved to be simultaneously reactive and stable.[12]

Figure 2:
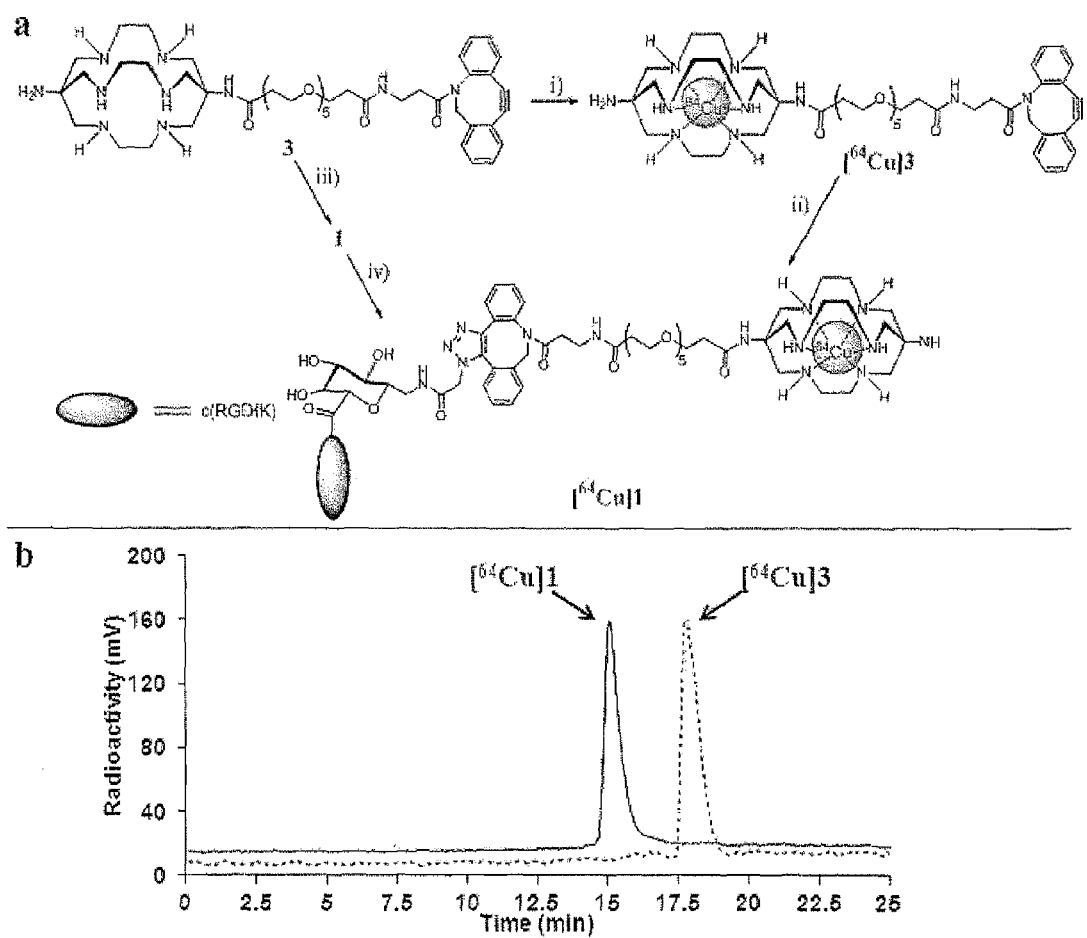
FIG. 2 shows the (a) Synthesis of [$^{64}$Cu]1. Reagents and conditions: (i) $^{64}$CuCl$_2$, 40° C., 0.4 M NH$_4$OAc; (ii) RGD peptide 2, 45° C., H$_2$O; (iii) RGD peptide 2, room temperature, H$_2$O; (iv) $^{64}$CuCl$_2$, 0.4 M NH$_4$OAc. (b) Radio-HPLC profiles of [$^{64}$Cu]1 and [$^{64}$Cu]3.

In one embodiment, a DiAmSar-containing dibenzocyclooctyne analog as a strained alkylne as well as a $^{64}Cu$ labeling precursor was built. A short polyethylene glycol) (PEG) linker was introduced between DiAmSar and dibenzocyclooctyne to fine-tune the in vivo pharmacokinetics of the resulting probes. Our synthesis started from commercially available dibenzocyclooctyne, which was coupled with a short PEG linker. After the activation of carboxylic acid group, the PEG-dibenzocyclooctyne was conjugated to commercially available DiAmSar in basic sodium borate buffer to afford 3 in 45% yield. Radiolabeling of 3 with $^{64}Cu$ was efficiently accomplished at 40° C. in 0.4 M NH$_4$OAc buffer within 30 min (FIG. 2a). The labeled product [$^{64}Cu$]3 was purified by HPLC. The radioactive peak containing [$^{64}Cu$]3 appeared at 17.67 min as shown in FIG. 2b. The specific activity of [$^{64}Cu$]3 was estimated to be 37 MBq nmol$^{-1}$.

The conjugations between 2 and [$^{64}Cu$]3 were carried out in deionized water and analyzed by analytical HPLC. When [$^{64}Cu$]3 (3.7 Mbq, 1 µM) was mixed with a large excess of 2 (>100 folds) at room temperature, [$^{64}Cu$]3 was rapidly consumed within 10-15 min, and [$^{64}Cu$]1 ($R_t$=15.05 min, FIG. 2b) formed in >92% radiochemical yield (Table 1, entries 1 and 2). With a small excess of 2 (5.7 folds), the radiochemical yield was decreased to 42% after combining 2 and [$^{64}Cu$]3 for 10 min at room temperature (entry 3). However, the elevated temperature (45° C.) significantly enhanced the [$^{64}Cu$]1 yield (>98%, entry 4) after 10-min mixing of 2 and [$^{64}Cu$]3. With prolonged reaction time (15 min), an excellent radiochemical yield (>98%) of [$^{64}Cu$]1 was still achieved by using 1.14:1 ratio of 2 and [$^{64}Cu$]3 (entry 5). Further reducing the concentration of 2 and [$^{64}Cu$]3 resulted in a low [$^{64}Cu$]1 yield (16%, entry 6). We also investigated the efficiency of the conjugation between 2 and [$^{64}Cu$]3 in PBS buffer. As shown in entry 7, [$^{64}Cu$]1 was formed in a quantitative yield at 45° C. within 15 min.

TABLE 1

Optimization of synthesis of [$^{64}$Cu]1 through the strain-promoted catalyst-free conjugation between 2 and [$^{64}$Cu]3.

| Entry | 2 | [$^{64}$Cu]3[a] | Solvent | Temperature | Reaction time/min | Radiochemical yield (%) |
|---|---|---|---|---|---|---|
| 1 | 228 μM | 3.7 MBq (1 μM) | H$_2$O | 25° C. | 15 | >98 |
| 2 | 114 μM | 3.7 MBq (1 μM) | H$_2$O | 25° C. | 10 | 92 |
| 3 | 5.7 μM | 3.7 MBq (1 μM) | H$_2$O | 25° C. | 10 | 42 |
| 4 | 5.7 μM | 3.7 MBq (1 μM) | H$_2$O | 45° C. | 10 | >98 |
| 5 | 1.14 μM | 3.7 MBq (1 μM) | H$_2$O | 45° C. | 15 | >98 |
| 6 | 0.29 μM | 1.85 MBq (0.5 μM) | H$_2$O | 45° C. | 10 | 16 |
| 7 | 1.14 μM | 3.7 MBq (1 μM) | PBS buffer | 45° C. | 15 | >98 |

[a]The concentration was estimated based on the specific activity of [$^{64}$Cu]3 (37 MBq nmol$^{-1}$), taking into account a correction of radioactive decay.

Figure 3:
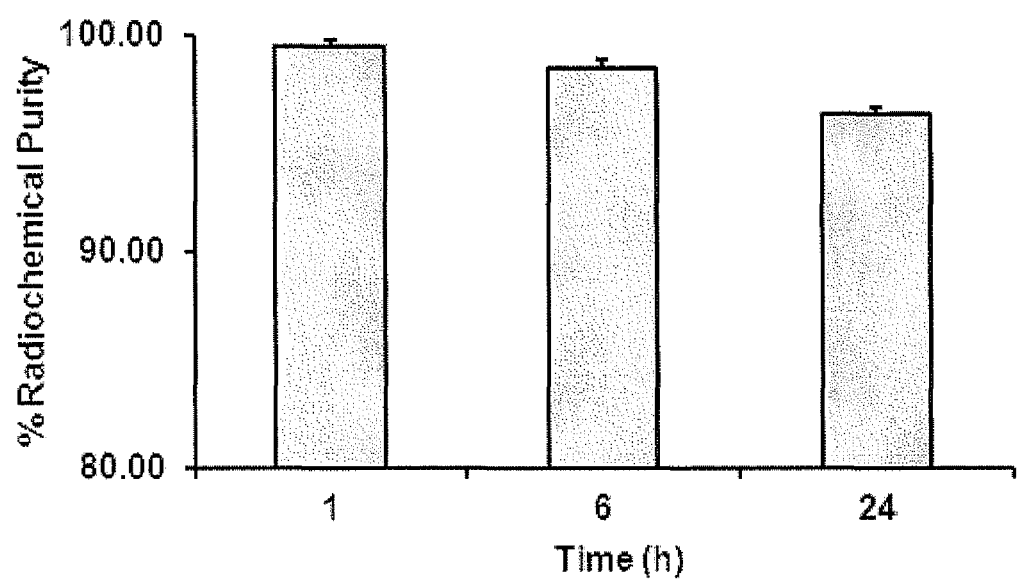
FIG. 3 shows the stability of [$^{64}$Cu]1 in PBS (pH=7.4) at room temperature for 1, 6, and 24 h.
Figure 4:
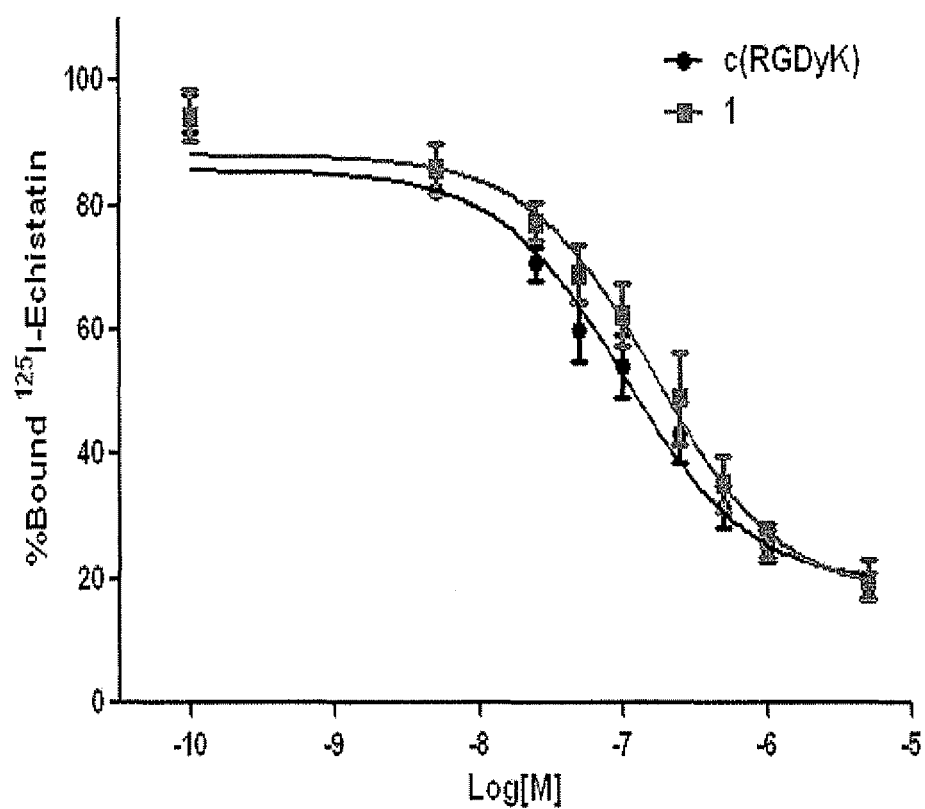
FIG. 4 shows the in vitro inhibition of $^{125}$I-echistatin bound to integrin $\alpha_v\beta_3$ on U87MG glioma cells by the non-modified peptide c(RGDyK) and peptide 1. The IC$_{50}$ values of c(RGDyK) and peptide 1 were calculated to be 105±5 nM and 170±3 nM, respectively.

The in vitro stability of [$^{64}$Cu]1 was evaluated in PBS buffer by radio-HPLC. Chromatographic results demonstrated no release of $^{64}$Cu from the conjugate over a period of 24 h (FIG. 3). This high stability is attributed to Sar cage in the conjugate. In addition, it is known that the U87MG cell line over-expresses integrin $\alpha_v\beta_3$ receptor [13]. Therefore, we used the U87MG cell line to measure the integrin $\alpha_v\beta_3$ binding affinity of 1 by a competitive cell-binding assay [13], where $^{125}$I-echistatin was employed as integrin $\alpha_v\beta_3$-specific radioligand for competitive displacement. The IC$_{50}$ values of c(RGDyK) and 1, which represent their concentrations required to displace 50% of the $^{125}$I-echistatin bound to the U87MG cells, were determined to be 105±5 nM and 170±3 nM, respectively (FIG. 4). The slightly decreased integrin $\alpha^v\beta_3$ binding of 1 as compared to c(RGDyK) indicates a minimum impact of a long tail (containing galactose, triazole, and Sar moieties) on the binding of c(RGDfK) to integrin $\alpha_v\beta_3$.

Figure 5:
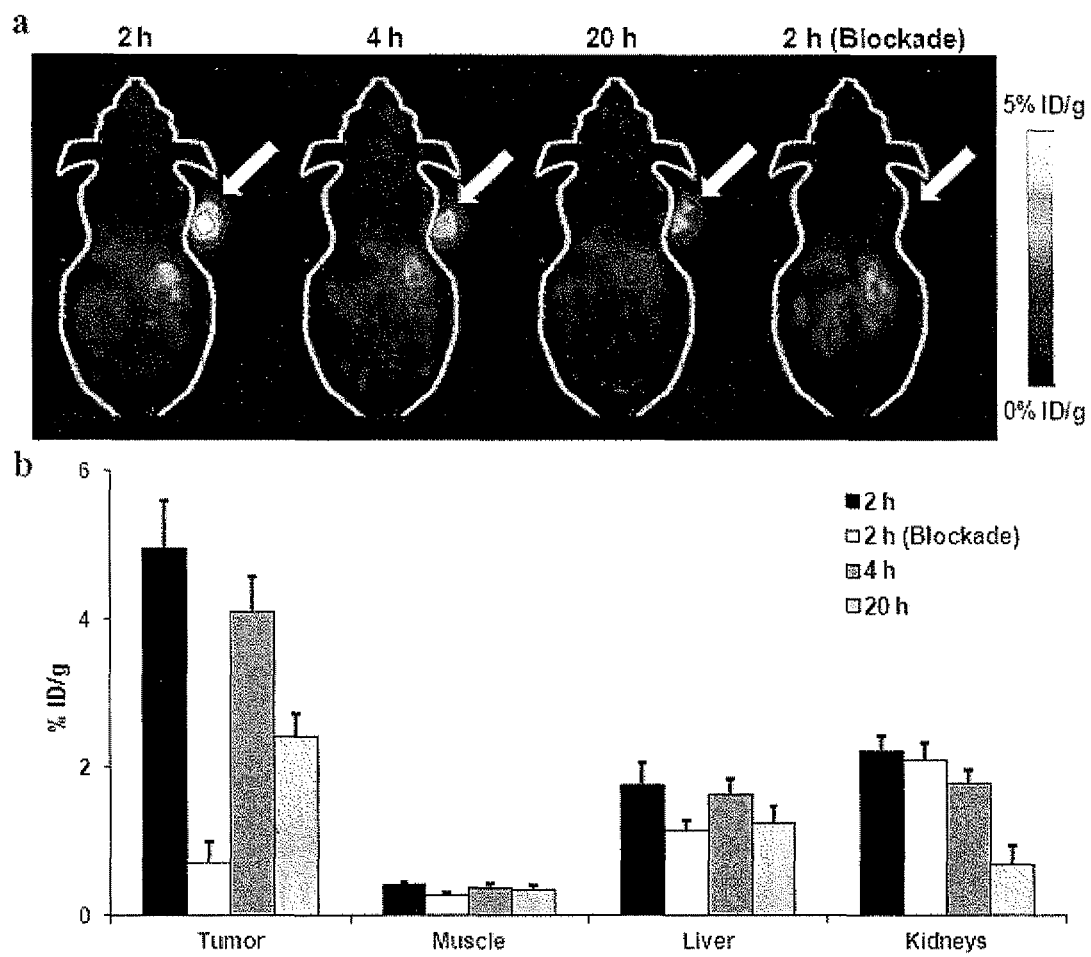
FIG. 5 shows (a) decay-corrected whole-body microPET images of U87MG tumor bearing mice (n=3) at 2, 4, 20 h after intravenous injection of [$^{64}$Cu]1. The image obtained with co-injection of c(RGDyK) (10 mg/kg body weight) is shown for 2 h blockade (right). Tumors are indicated by arrows. (b) MicroPET quantification of tumors and major organs at 2, 4, and 20 h after intravenous injection of [$^{64}$Cu]1. The blockade with co-injection of c(RGDyK) (10 mg/kg body weight) is only shown at 2 h post injection.
Figure 6:
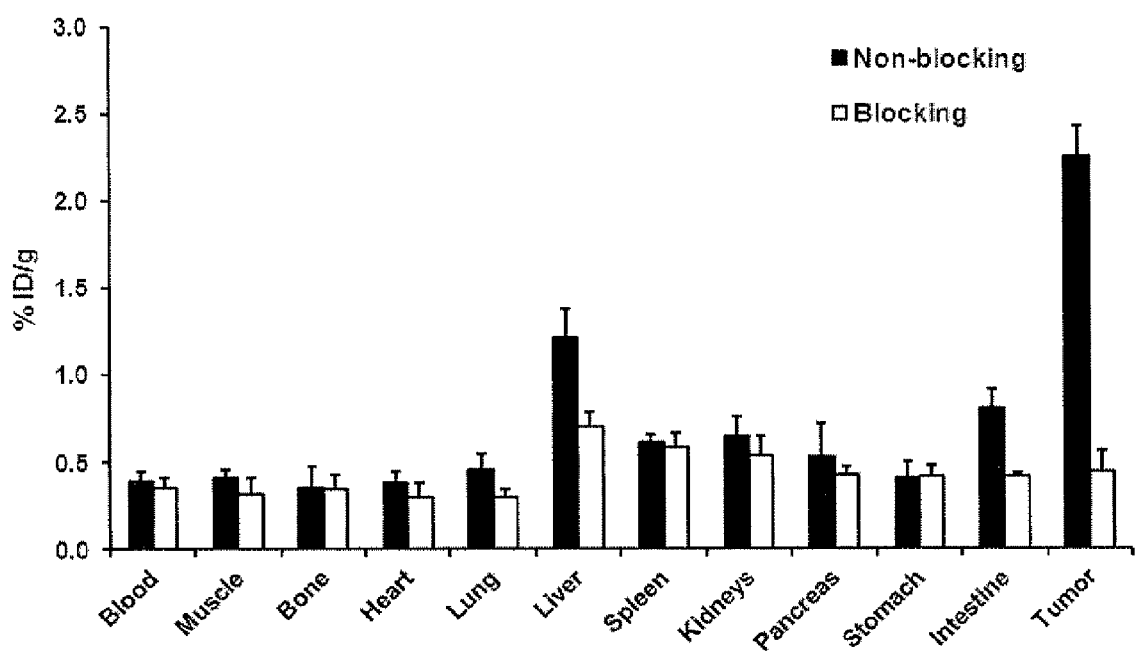
FIG. 6 shows the biodistribution of [$^{64}$Cu]1 in U87MG tumor bearing athymic nude mice at 20 h with and without co-injection of 10 mg/kg of c(RGDyK) as a blocking agent (n=3/group).

The in vivo tumor-targeting efficacy of [$^{64}$Cu]1 was evaluated in nude mice bearing U87MG human glioma xenograft tumors (n=3) by static microPET scans at 2, 4, and 20 h after tail-vain injection of [$^{64}$Cu]1. Representative decay-corrected coronal images at different time points were shown in FIG. 5a. U87MG tumors were clearly visualized at all time points examined. Region-of-interest (ROI) analysis on microPET images showed the tumor uptake values were 4.96±0.65, 4.11±0.48, and 2.41±0.31% ID/g at 2, 4, and 20 h post injection, respectively (FIG. 5b). At 2 h post injection, the tumor/liver, tumor/kidneys, and tumor/muscle ratios reached 2.82±0.76, 2.22±1.49, and 11.79±2.65, respectively. Consequently, the high tumor-to-nontumor ratios provided excellent contrast for PET imaging. Blocking experiment was conducted to confirm the integrin $\alpha_v\beta_3$ specificity of [$^{64}$Cu]1. In the presence of a blocking dose (10 mg/kg) of c(RGDyK), the U87MG tumor uptake was reduced to the background level (0.71±0.28% ID/g) at 2 h post injection (FIGS. 5a and 5b). The uptake values of normal organs (e.g., liver, kidneys, and muscle) were also lower than those without coinjection of c(RGDyK) (FIG. 5b). The ex vivo biodistribution of [$^{64}$Cu]1 was examined in U87MG tumor-bearing mice at 20 h pi with and without coinjection of c(RGDyK). The results were consistent with the quantitative analysis of PET imaging (FIG. 6).

The following Examples are provided in order to demonstrate and further illustrate certain embodiments and aspects of the present invention and are not to be construed as limiting the scope thereof.

Synthesis of Peptide 2

The synthesis of Peptide 2 (shown below) is summarized in Scheme 1.

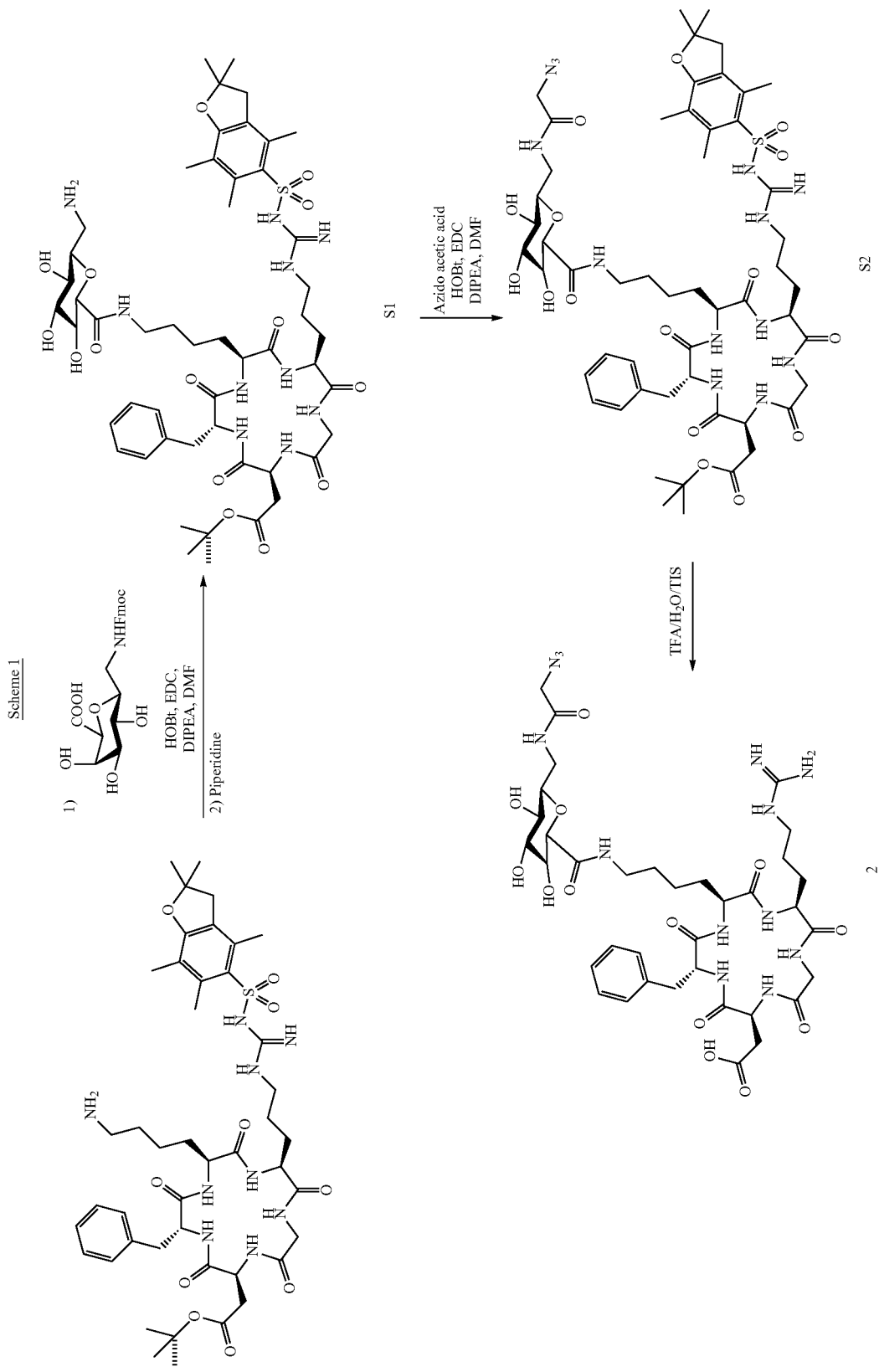
Scheme 1

Preparation of Peptide S1

To a solution of (3R,4R,5S,6S)-6-((((9H-fluoren-9-yl) methoxy)carbonylamino)methyl)-3,4,5-trihydroxytetrahydro-2H-pyran-2-carboxylic acid (301 mg, 0.702 mmol, 1.2 equiv) in DMF (5 mL) was added HOBt (95 mg, 0.702 mmol, 1.2 equiv) and EDC (135 mg, 0.702 mmol, 1.2 equiv). The mixture was stirred at room temperature for 2 hrs. The protected c(RGDfK) TFA salt (600 mg, 0.585 mmol, 1.0 equiv) and DIPEA (0.204 mL, 1.169 mmol, 2 equiv) in DMF (5 mL) was added to the reaction dropwise. The mixture was stirred overnight. To the mixture was then added EtOAc (160 mL), ultrasonicated for 30 min, and cooled to 0° C. A white solid precipitated from the solution. The solid was filtered, washed with water (10 mL) and ether (20 mL×2), and dried. To a round bottom flask containing the solid (650 mg, 0.491 mmol, 1 equiv) was added piperidine (2.15 g, 25.2 mmol). After overnight stirring, the reaction was concentrated under vacuum to remove piperidine. Acetonitrile (20 mL×3) was added to facilitate co-evaporation. The residue was dried under vacuum for 2 hrs. The white solid residue was then washed with ether (20 mL×3) under ultrasound. The residue solid was filtered and dried under vacuum overnight to afford peptide S1 (560 mg) in a total of 90% yield. $^1$H NMR (d$_6$-DMSO, 400 MHz), δ: 8.42 (t, 1H), 8.08-8.06 (m, 2H), 8.02-7.98 (d, 3H), 7.60 (t, 1H), 7.43 (t, 1H), 7.51 (d, 1H), 7.26-7.11 (m, 6H), 4.72 (d, 1H), 4.59 (q, 1H), 4.51 (d, 1H), 4.42 (q, 1H), 4.10 (m, 1H), 4.00 (dd, 1H), 3.95-3.85 (m, 2H), 3.72 (s, 1H), 3.76-3.70 (m, 2H), 3.25-3.20 (m, 2H), 3.05-2.87 (m, 9H), 2.83-2.75 (m, 1H), 2.65-2.55 (m, 3H), 2.47-2.33 (m, 8H), 1.97 (s, 3H), 1.65-1.48 (m, 2H), 1.40-1.20 (m, 20H), 0.97-0.95 (m, 2H). ESI-MS: calculated for $C_{51}H_{76}N_{10}O_{15}S$: 1100.52; found: 1101.4 [M+H]$^+$.

Preparation of Peptide S2

To a solution of azido acetic acid (5.65% solution in DCM/THF, 1.56 g, 0.872 mmol, 2.5 equiv) in DMF (2 mL), was added HOBt (118 mg, 0.872 mmol, 2.5 equiv) and EDC (167 mg, 0.872 mmol, 2.5 equiv). The mixture was stirred at room temperature for 20 min. Peptide S1 (400 mg, 0.349 mmol, 1 equiv) in DMF (7.5 vol) was added along with DIPEA (0.152 mL, 0.872 mmol, 2.5 equiv) to the above mixture. The reaction was stirred at room temperature for additional 20 min. The reaction was quenched by addition of water (few drops). DMF was removed under vacuum. Acetonitrile (15 mL×3) was added to facilitate co-evaporation of DMF. To the residue was added water (90 mL) and treated with ultrasound for 30 min. The white solid precipitate was collected by filtration. The cake was washed with mother liquid (20 mL×1), ether (15 mL×2), and dried under vacuum with $P_2O_5$ overnight to afford peptide S2 (392 mg, 92% yield). $^1$H NMR (d$_6$-DMSO, 400 MHz), δ: 8.42 (t, 1H), 8.11-8.05 (m, 2H), 8.00 (d, 2H), 7.50 (d, 1H), 7.43 (t, 1H), 7.26-7.11 (m, 5H), 4.92 (d, 1H), 4.78 (d, 1H), 4.59-4.53 (m, 2H), 4.42 (q, 1H), 4.10 (m, 1H), 4.00 (dd, 1H), 3.95-3.85 (m, 2H), 3.82 (d, 2H), 3.76-3.70 (m, 2H), 3.25-3.20 (m, 2H), 3.05-2.87 (m, 9H), 2.83-2.75 (m, 1H), 2.65-2.55 (m, 1H), 2.47-2.33 (m, 8H), 1.97 (s, 3H), 1.65-1.48 (m, 2H), 1.40-1.20 (m, 20H), 0.97-0.95 (m, 2H). ESI-MS: calculated for $C_{53}H_{77}N_{13}O_{16}$: 1183.53. found: 1184.4 [M+H]$^+$.

Preparation of Peptide 2

To peptide S2 (40 mg, 0.034 mmol, 1 equiv) was added 2 mL of the following solvents TFA:TIS:H$_2$O=95:2.5:2.5. The reaction was stirred at room temperature for 30 min. To the mixture was added cold ether (25 mL). The precipitate was formed and concentrated after centrifugation. The precipitate was filtered and washed with cold ether (2 mL×3) to afford peptide 2 (23.5 mg, 67% yield). $^1$H NMR (D$_2$O, 400 MHz), δ: 7.18-7.07 (m, 5H), 4.55 (dd, 1H), 4.45 (dd, 1H), 4.16 (dd, 1H), 4.07 (dd, 1H), 4.01 (d, 1H), 3.95 (s, 1H), 3.86 (s, 2H), 3.71 (dd, 1H), 3.56-3.52 (m, 2H), 3.39-3.26 (m, 4H), 3.04-2.99 (m, 4H), 2.90-2.70 (m, 3H), 2.53 (dd, 1H), 1.71-1.64 (m, 1H), 1.51-1.46 (m, 2H), 1.37-1.32 (m, 3H), 1.27-1.18 (m, 2H), 0.85-0.78 (m, 2H). $^{13}$C NMR (D$_2$O, 100 MHz), δ: 174.7, 174.5, 173.2, 172.9, 171.5, 171.4, 170.9, 170.7, 156.8, 136.1, 129.3, 128.9, 127.4, 78.1, 77.7, 73.5, 69.6, 68.0, 55.5, 55.1, 52.5, 52.1, 49.7, 43.6, 40.6, 40.4, 38.7, 37.1, 34.4, 30.0, 27.8, 27.4, 24.6, 22.6. ESI-MS: calculated for $C_{38}H_{54}F_3N_{13}O_{15}$: 989.38. found: 876.4 [M-CF$_3$COOH+H]$^+$.

Synthesis of 3

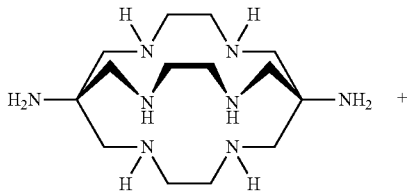

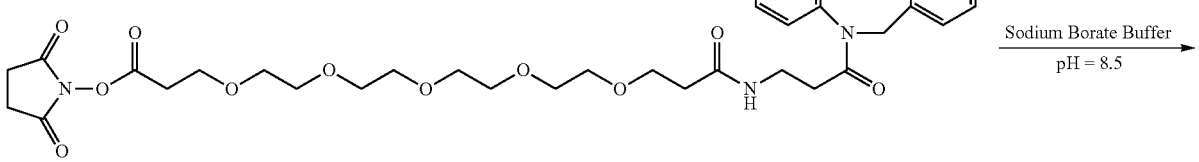

Sodium Borate Buffer
pH = 8.5

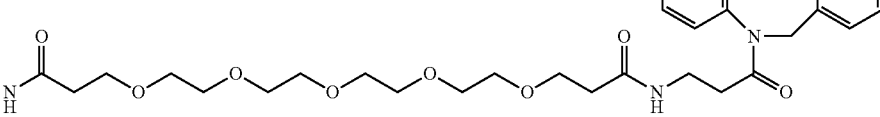

3

To the solution of 1,8-diamino-3,6,10,13,16,19-hexaazabicyclo[6.6.6]-eicosine (1 mg, 2.47 μmol, 1 equiv) in 200 uL of sodium borate buffer (pH 8.5) was added S3 (2 mg, 2.88 μmol, 1.17 equiv) in 10 uL of DMSO. The mixture was incubated at room temperature for 2 h and purified by semi-preparative HPLC. The desired peak was collected and concentrated to afford 3 as a white powder (1.0 mg, 45%). ESI-MS: calculated for $C_{46}H_{72}N_{10}O_8$: 893.1.3. found: 894.0 $[M+H]^+$.

Synthesis of 1

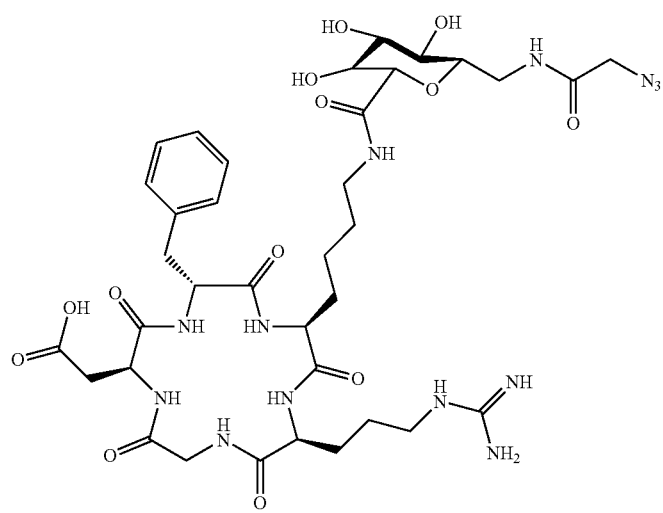

2

+

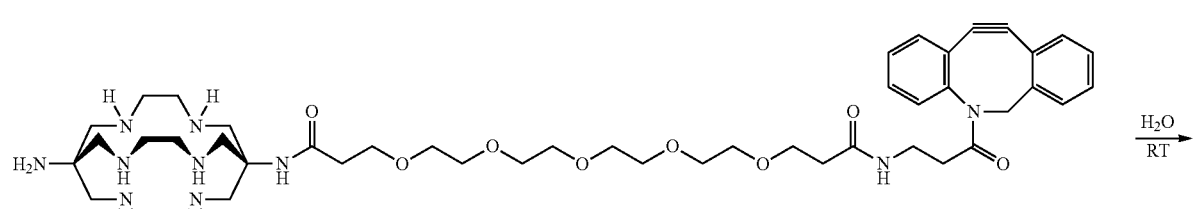

3

-continued

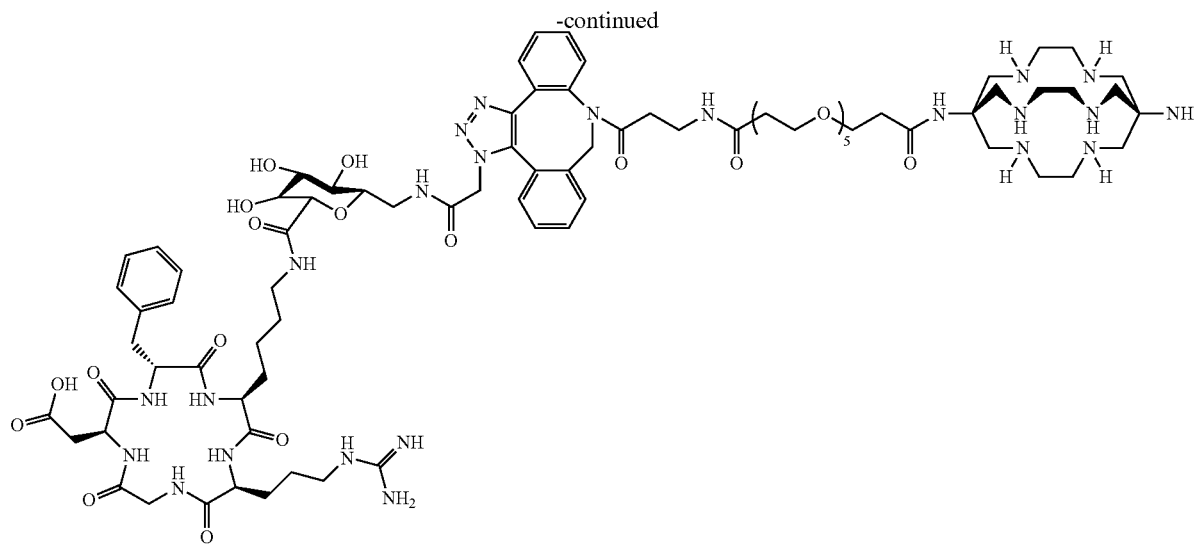

1

To the solution of 3 (0.9 mg, 1.01 μmol, 1 equiv) in 30 uL of deionized water was added 2 (0.973 mg, 1.11 μmol, 1.1 equiv) in 20 uL of deionized water. The mixture was incubated at room temperature for 1 h and purified by semi-preparative HPLC. The desired peak was collected, concentrated, and lyophilized to afford 1 as a white powder (1.7 mg, 95%). ESI-MS: calculated for $C_{82}H_{125}N_{23}O_{21}$: 1769.01. found: 1770.21 $[M+H]^+$, 885.43 $[M+2H]^{2+}$, 590.90 $[M+3H]^{3+}$.

Radiosynthesis of [$^{64}$Cu]3

[$^{64}$Cu]Cu(OAc)$_2$ was prepared by adding 37-111 MBq of [$^{64}$Cu]CuCl$_2$ in 0.1 N HCl into 300 μL of 0.4 M ammonium acetate buffer (pH=5.5), followed by mixing and incubating for 15 min at room temperature. The [$^{64}$Cu]Cu(OAc)$_2$ solution (37-111 MBq) was then added into a solution of 3 (5 μg precursor per mCi $^{64}$Cu) dissolved in 0.4 M NH$_4$OAc (pH=5.5) solution. The reaction mixture was incubated at 40° C. for 30 min. The labeled product was then purified by analytical HPLC. The radioactive peak containing desired product (Rt=17.67 min) was collected and concentrated by

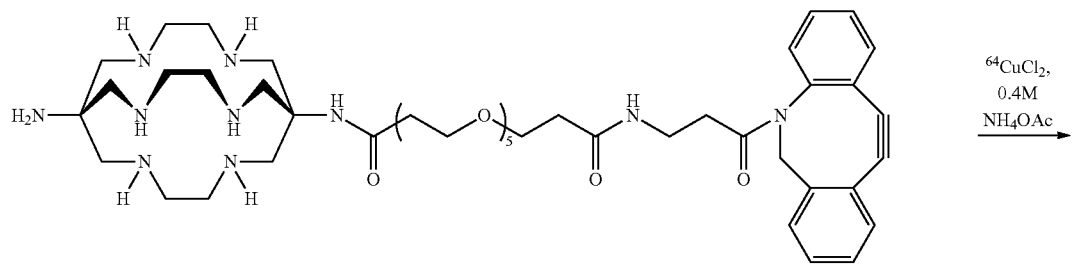

3

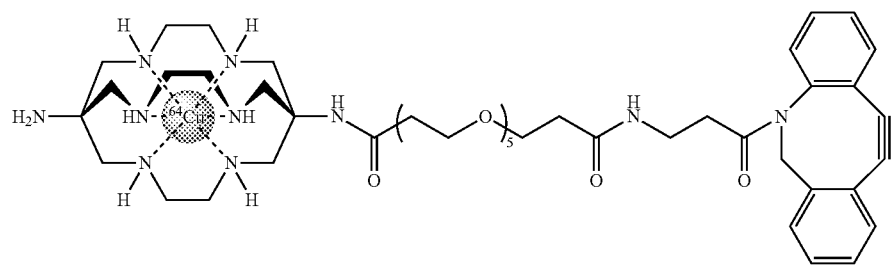

[$^{64}$Cu]3 rotary evaporation to afford [$^{64}$Cu]3. The product was reconstituted in deionized water for use in following experiments. The specific activity of [$^{64}$Cu]3 was estimated to be 37 MBq nmol$^{-1}$.

Radiosynthesis of [$^{64}$Cu]1: "Click" Coupling of 2 and [$^{64}$Cu]3 into a sterile dose vial for use. The specific activity of [$^{64}$Cu]1 was estimated to be 30 MBq nmol$^{-}$.

Experimental Methods

General Materials and Methods.

All chemicals and solvents were obtained from Aldrich (Milwaukee, Wis., USA) and used without further purifica-

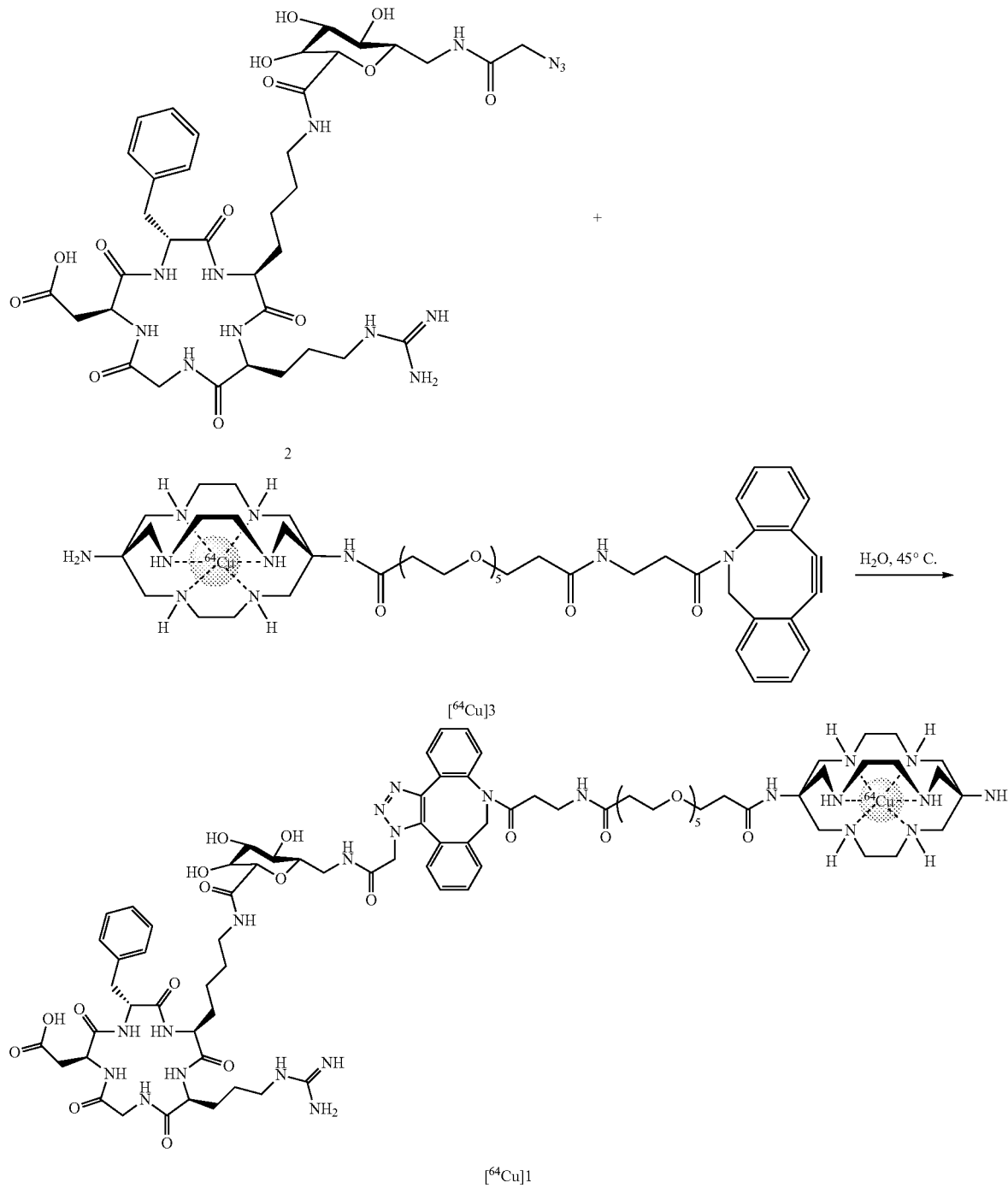

To the solution of [$^{64}$Cu]3 (37 MBq) in 50 uL of deionized water was added 2 (1.14 equiv) in 50 uL of deionized water. The reaction mixture was incubated at 45° C. for 15 min to afford [$^{64}$Cu]1. The product was then reconstituted in 500-800 μL PBS, and passed through a 0.22-μm Millipore filter tion. 1,8-Diamino-3,6,10,13,16,19-hexaazabicyclo[6.6.6]-eicosine was purchased from Areva Med (Dallas, Tex.). $^{125}$I-Echistatin was obtained from Perkin-Elmer (Waltham, Mass.). $^{1}$H and $^{13}$C nuclear magnetic resonance (NMR) were recorded on a Varian 400 MHz spectrometer. Mass spectrum was obtained on a ThermoElectron Finnigan LTQ mass spectrometer equipped with an electrospray ionization (ESI) source (Thermo Scientific, USA). HPLC analyses were carried out on an analytical reversed-phase high performance liquid chromatography (HPLC) system equipped with a dual UV absorbance detector (Waters 2487) using a phenomenex C18 RP (250×4.6 mm 5 micron). The flow was 1 mL/min, with the mobile phase starting from 100% solvent A (0.1% TFA in water), followed by a gradient mobile phase to 20% solvent A and 80% solvent B (0.1% TFA in acetonitrile) at 30 min. The UV absorbance was monitored at 214 nm and the identification of the peptides was confirmed based on the UV spectrum using a PDA detector. The radioactivity was detected by a model of Ludlum 2200 single-channel radiation detector. The stability study was performed under the same HPLC condition. MicroPET scans were performed on a microPET R4 rodent model scanner (Siemens Medical Solutions USA, Inc., Knoxville, Tenn.). The scanner has a computer-controlled bed and 10.8-cm transaxial and 8-cm axial fields of view (FOVs). It has no septa and operates exclusively in the 3-dimensional (3D) list mode. Animals were placed near the center of the FOV of the scanner.

Statistical Analysis.

Quantitative data were expressed as mean±SD. Means were compared using one-way ANOVA and student's t-test. P values<0.05 were considered statistically significant.

Partition Coefficient.

The partition coefficient value was expressed as log P. Log P of [$^{64}$Cu]1 was determined by measuring the distribution of radioactivity in 1-octanol and PBS. Approximately 111 kBq of [$^{64}$Cu]1 in 2 μL of PBS (pH=7.4) was added to a vial containing 0.5 mL 1-octanol and 0.5 mL of PBS (pH=7.4). After vigorously vortexing for 10 min, the vial was centrifuged at 12,500 rpm for 5 min to ensure the complete separation of layers. 200 μL of each layer was pipetted into test tubes, and radioactivity was measured using a gamma counter (Perkin-Elmer Packard Cobra). The mean value was calculated from triplicate experiments. The log P value of [$^{64}$Cu]1 was determined to be 4.94±0.10.

Probe Stability Determination.

The stability of [$^{64}$Cu]1 was tested in PBS. In brief, 3.7 MBq of the [$^{64}$Cu]1 was pipetted into 0.5 mL of the PBS and incubated in PBS at room temperature. At various time points (1, 6, and 24 h), an aliquot of the solution was taken and the radiochemical purity was determined by reverse-phase HPLC under identical conditions. The parent [$^{64}$Cu]1 was determined to be >99%, 98%, and 96% at 1, 6, and 24 h, respectively.

Cell Culture.

U87MG human glioblastoma cell line was obtained from the American Type Culture Collection (ATCC, Manassas, Va.). U87MG glioma cells were grown in Dulbecco's modified medium (USC Cell Culture Core, Los Angeles, Calif.) supplemented with 10% fetal bovine serum (FBS) at 37° C. in humidified atmosphere containing 5% $CO_2$.

Integrin $\alpha_v\beta_3$ Receptor Binding Assay.

U87MG cells were suspended with binding buffer [25 mM 2-amino-2-(hydroxymethyl)-1,3-propanediol, hydrochloride (Tris-HCl), pH 7.4, 150 mM NaCl, 1 mM $CaCl_2$, 0.5 mM $MgCl_2$, 1 mM $MnCl_2$, and 0.1% bovine serum albumin (BSA)]. Incubation was conducted in a 96-well plate with a total volume of 200 μL in each well containing 2×10$^5$ cells, 0.02 μCi (0.74 kBq) $^{125}$I-echistatin (Perkin-Elmer), and 0-5000 nM of c-(RGDyK) or peptide 1 for 3 h on a shaker at room temperature. After incubation, cells were washed three times with cold phosphate buffered saline (PBS) with 0.1% BSA. Thereafter, the plate was heated to 40° C. and dried. The dried filter membranes were punched off from the wells and collected in polystyrene culture test tubes. Cell bound radioactivity was then measured using a gamma counter (Perkin-Elmer Packard Cobra). The $IC_{50}$ values were calculated by nonlinear regression analysis using the GraphPad Prism computer-fitting program (GraphPad Software, Inc., San Diego, Calif.). Each data point is a result of the average of duplicate wells.

Animal Model.

All animal studies were approved by the University of Southern California Institutional Animal Care and Use Committee. Female athymic nude mice (about 4-6 weeks old, with a body weight of 20-25 g) were obtained from Harlan Laboratories (Livermore, Calif.). The U87MG human glioma xenograft model was generated by subcutaneous injection of 5×10$^6$ U87MG human glioma cells into the front flank of female athymic nude mice. The tumors were allowed to grow 3-5 weeks until 200-500 mm$^3$ in volume. Tumor growth was followed by caliper measurements of the perpendicular dimensions.

MicroPET Imaging and Blocking Experiment.

MicroPET scans and imaging analysis were performed using a rodent scanner (microPET R4 scanner; Siemens Medical Solutions). About 7.4 MBq of [$^{64}$Cu]1 was intravenously injected into each mouse (n=3) under isoflurane anesthesia. Five-minute static scans were acquired at 2, 4, and 20 h pi. The images were reconstructed by a two-dimensional ordered-subsets expectation maximum (OSEM) algorithm. For each microPET scan, regions of interest were drawn over the tumor, normal tissue, and major organs on the decay-corrected whole-body coronal images. The radioactivity concentration (accumulation) within the tumor, muscle, liver, and kidneys were obtained from the mean value within the multiple regions of interest and then converted to % ID/g. For the blocking experiment, mice bearing U87MG tumors were scanned (5 min static) at 2, 4, and 20 h after the co-injection of 7.4 MBq of [$^{64}$Cu]1 with 10 mg/kg c(RGDyK) peptide per mouse.

Biodistribution Studies.

The U87MG tumor bearing mice (n=3) were injected with 7.4 MBq of [$^{64}$Cu]1. At 20 h after intravenous injection of [$^{64}$Cu]1, mice were sacrificed and dissected. Blood, U87MG tumor, major organs, and tissues were collected and weighed wet. The radioactivity in the tissues was measured using a gamma counter (Perkin-Elmer Packard Cobra). The results were presented as percentage injected dose per gram of tissue (% ID/g). For each mouse, the radioactivity of the tissue samples was calibrated with a known aliquot of the injected activity. Mean uptake (% ID/g) for a group of animals was calculated with standard deviations.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Those skilled in the art will recognize, or be able to ascertain using no more than routine experimentation, many equivalents to the specific embodiments of the method and compositions described herein. Such equivalents are intended to be encompassed by the following claims.

REFERENCES

The following references are incorporated herein in the entirety:

[1] Chen K and Chen X. Positron emission tomography imaging of cancer biology: current status and future prospects. Semin Oncol 2011; 38:70-86.
[2] Chen K and Conti P S. Target-specific delivery of peptide-based probes for PET imaging. Adv Drug Deliv Rev 2010; 62:1005-22.
[3] Zeglis B M and Lewis J S. A practical guide to the construction of radiometallated bioconjugates for positron emission tomography. Dalton Trans 2011; 40:6168-95.
[4] Hao G, Singh A N, Oz O K, and Sun X. Recent advances in copper radiopharmaceuticals. Curr Radiopharm 2011; 4:109-21.
[5] Kolb H C and Sharpless K B. The growing impact of click chemistry on drug discovery. Drug Discov Today 2003; 8:1128-37.
[6] Nwe K and Brechbiel M W. Growing applications of "click chemistry" for bioconjugation in contemporary biomedical research. Cancer Biother Radiopharm 2009; 24:289-302.
[7] Debets M F, van Berkel S S, Dommerholt J, Dirks A T, Rutjes F P, and van Delft F L. Bioconjugation with strained alkenes and alkynes, Acc Chem Res 2011; 44:805-15.
[8] Haubner R, Beer A J, Wang H, and Chen X. Positron emission tomography tracers for imaging angiogenesis. Eur J Nucl Med Mol Imaging 2010; 37 Suppl 1:S86-103.
[9] Haubner R, Wester H J, Burkhart F, Senekowitsch-Schmidtke R, Weber W, Goodman S L, et al. Glycosylated RGD-containing peptides: tracer for tumor targeting and angiogenesis imaging with improved biokinetics. J Nucl Med 2001; 42:326-36.
[10] Liu W, Hao G, Long M A, Anthony T, Hsieh J T, and Sun X. Imparting multivalency to a bifunctional chelator: a scaffold design for targeted PET imaging probes. Angew Chem Int Ed Engl 2009; 48:7346-9.
[11] Liu S, Li Z, Yap L P, Huang C W, Park R, and Conti P S. Efficient preparation and biological evaluation of a novel multivalency bifunctional chelator for 64Cu radiopharmaceuticals. Chemistry 2011; 17:10222-5.
[12] Debets M F, van Berkel S S, Schoffelen S, Rutjes F P, van Hest J C, and van Delft F L. Aza-dibenzocyclooctynes for fast and efficient enzyme PEGylation via copper-free (3+2) cycloaddition. Chem Commun (Camb) 2010; 46:97-9.
[13] Zhang X, Xiong Z, Wu Y, Cai W, Tseng J R, Gambhir S S, et al. Quantitative PET imaging of tumor integrin alphavbeta3 expression with 18F-FRGD2. J Nucl Med 2006; 47:113-21.

What is claimed is:

1. A compound according to Formula III:

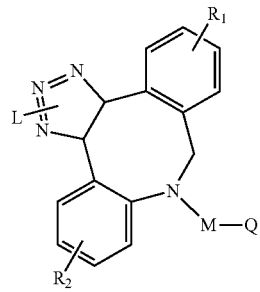

Formula III wherein L is bound to any of the nitrogen atoms of the triazole moiety, wherein L comprises a peptide, the moiety M comprises a moiety selected from the group consisting of one or more polyethylene glycol units and one or more sugars, the moiety Q comprises a hexaazamacrobicyclic sarcophagine chelator capable of coordinating a radiometal nuclide, and the benzene rings may be mono-, di-, tri-, or tetra-substituted with $R_1$ and $R_2$ groups selected from the group consisting of H, halide, hydroxy, alkyl, aryl, nitro or amine groups.

2. A rapid, efficient, and catalyst-free click chemistry method for generating radiometal-labeled probes for imaging and therapy comprising: reacting an azido composition, $N_3$-L of Formula I with a strained alkyne of Formula II in the absence of a catalyst, according to the following reaction:

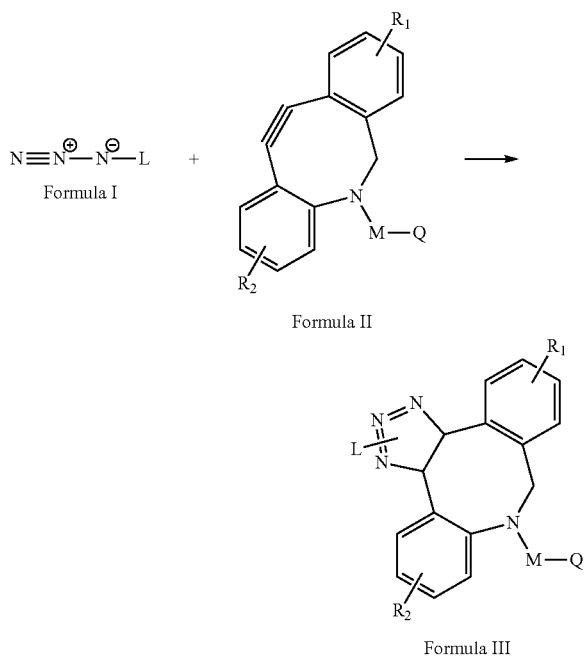

Formula I

Formula II

Formula III wherein L is bound to any of the nitrogen atoms of the triazole moiety, wherein L comprises a peptide, the moiety M comprises a moiety selected from the group consisting of one or more polyethylene glycol units and one or more sugars, the moiety Q comprises a hexaazamacrobicyclic sarcophagine chelator capable of coordinating a radiometal nuclide, and the benzene rings may be mono-, di-, tri-, or tetra-substituted with $R_1$ and R2 groups selected from the group consisting of H, halide, hydroxy, alkyl, aryl, nitro or amine groups.

3. The method according to claim 2, wherein the chelator Q is chelated to a radiometal nuclide selected from the group consisting of $^{61}$Cu, $^{62}$Cu, $^{64}$Cu, $^{67}$Cu, $^{68}$Ga, $^{86}$Y, and $^{89}$Zr.

4. The method of claim 2, wherein the peptide is an RGD peptide.

5. The method of claim 4, wherein Q is 3,6,10,13,16,19-hexaazabicyclo[6.6.6]eicosane-1,8-diamine.

6. The method of claim 2, wherein the groups $R_1$ and $R_2$ are all hydrogen and the radionuclide is $^{64}Cu$.

7. The method of claim 2, wherein L is an RGD peptide, M is PEG, Q is 3,6,10,13,16,19-hexaazabicyclo[6.6.6]eicosane-1,8-diamine ("DiAmSar"), the groups $R_1$ and $R_2$ are all hydrogen and the radionuclide is $^{64}Cu$.

* * * * *